United States Patent [19]

Murphy et al.

[11] Patent Number: 4,518,387

[45] Date of Patent: May 21, 1985

[54] SYRINGE INJECTION APPARATUS WITH ADJUSTABLE DOSAGE INDICATOR

[76] Inventors: Frank Murphy, 285 Channelwood Cir., Apartment 506, Akron, Ohio 44307; William F. Peterson, 2650 Eleventh St., Cuyahoga Falls, Ohio 44221

[21] Appl. No.: 453,601

[22] Filed: Dec. 27, 1982

[51] Int. Cl.³ .............................................. A61M 5/00
[52] U.S. Cl. ..................................... 604/187; 604/115
[58] Field of Search ............. 604/187, 198, 207, 208, 604/211, 407, 117, 115, 192, 196, 197, 263

[56] References Cited

U.S. PATENT DOCUMENTS

| | | | |
|---|---|---|---|
| 2,047,010 | 7/1936 | Dickinson | 604/117 X |
| 2,390,246 | 12/1945 | Folkman | 604/211 |
| 2,660,169 | 11/1953 | Malm | 604/115 X |
| 3,122,280 | 2/1964 | Goda | 604/211 |
| 4,153,056 | 5/1979 | Silver et al. | 604/211 |
| 4,219,055 | 8/1980 | Wright | 604/407 |

FOREIGN PATENT DOCUMENTS 1022758  1/1958  Fed. Rep. of Germany ...... 604/117

*Primary Examiner*—John D. Yasko
*Attorney, Agent, or Firm*—Oldham, Oldham & Weber Co.

[57] ABSTRACT

An invention which allows the patient to self-inject himself. The invention serves as a two-fold unit. First, the invention allows the patient to measure out the exact amount of medical fluid to be used. Secondly, the invention allows the patient to inject himself with a minimum amount of discomfort or pain without having to remove the syringe from the apparatus.

6 Claims, 17 Drawing Figures

SYRINGE INJECTION APPARATUS WITH ADJUSTABLE DOSAGE INDICATOR

TECHNICAL FIELD

This application relates to the field of self-adjusting syringe apparatus. For many years there have been devices which measure the dosage or devices which inject the syringe into the patient, but not one that did both. This invention incorporates both dosage and injection into one while making the injection virtually painless to the patient due to the unique design of the injecting head.

BACKGROUND ART

Heretofore, prior art has taught devices for measuring out dosages or devices for injecting patients. U.S. Pat. Nos. 3,840,011 to Wright; 3,875,979 to Hults; 3,610,241 to LeMarie; 4,248,225 to Moore; 3,833,030 to Waldbauer; and 4,252,159 to Maki, all teach a dosage metering and/or indicating device. U.S. Pat. Nos. 4,022,207 to Citrin; 4,173,225 to Newman; 3,720,211 to Kyrias; 4,178,928 to Tischlinger; and 4,085,748 to Boyer all teach an injection device. U.S. Pat. No. D 247,576 to Ekbert teaches a particular design for an injecting pistol.

The invention disclosed here does not resemble the artistic structure of Ekbert U.S. Pat. No. D 247,576.

U.S. Pat. No. 3,720,211 to Kyrias teaches an electrically driven solenoid actuated device for syringe injection into the patient. U.S. Pat. No. 4,173,225 to Newman teaches a spring-loaded syringe injection device. U.S. Pat. No. 4,022,207 to Citrin teaches a ratchet mechanism device to inject the syringe. U.S. Pat. No. 4,085,748 to Boyer teaches a sliding plate injection system activated by a band member to inject the syringe. U.S. Pat. No. 4,178,928 to Tischlinger teaches a spring-loaded injection system to inject the syringe. The present invention is unlike prior mechanisms whereas this invention incorporates a unique structure to tension the skin during the injection to ease pain, a unique cartridge loading system, and mechanism to provide a slight vacuum at insertion to determine if the needle is properly located.

Further, this invention differs from prior art in the field of dosage measuring devices, those being U.S. Pat. Nos. 3,833,030 to Waldbauer; 3,840,011 to Wright; 3,875,979 to Hults; 3,610,241 to LeMarie; 4,248,225 to Moore; and 4,252,159 to Maki in its structural and its functioning mode and the fact that the dosage measuring device is also an injection device.

DISCLOSURE OF INVENTION

It is an aspect of the present invention to enable the user to self-inject himself with the use of only one hand.

It is another aspect of the present invention to allow the user to self-administer the injection in difficult areas, where assistance by another person was needed in the past.

Yet another aspect of the present invention is a needle guide which prevents the needle from bending or breaking during the injection or loading process, even through scar tissue.

Still another aspect of the invention is a needle guide which pulls the skin taut, enabling the injection into the skin with minimal discomfort.

Yet another aspect of the invention is the presetting capabilities of the device which aids persons incapable of setting the device by themselves to administer correct dosage.

Still another aspect of the invention is to enable the user to self-inject himself virtually anywhere on his person and at any angle.

Yet another aspect of the invention is the base platform which enables the invention to be stored in an upright position.

Still another aspect of the invention is the unique visual and manual cam action of the piston assembly which enables the user to detect blood, assuring safe injection into adipose tissue.

Yet another aspect of the invention is an auxiliary stop which enables the user to administer several different medications out of the same syringe.

Still another aspect of the invention is a vial adapter which allows maximum usage of medication from the vial while also minimizing the needle protrusions into the vial itself.

Yet another aspect of the invention is it eliminates the need for visiting nurses formerly necessary to administer the dosage.

These and other aspects of the present invention which will become more apparent as the detailed description proceeds are achieved by: a manual syringe injection apparatus, comprising a cylindrical tube; a cylindrical needle guide attached to said tube by a sliding means at on end of said tube; an elevator ejector attached to said tube in the center section of said tube; and a piston assembly inserted inside of the other end of said tube, wherein a syringe is locked into said tube by said elevator ejector.

BRIEF DESCRIPTION OF DRAWINGS

FIG. 6 illustrates an assembly comprising an elevator pusher shown in 6A, an elevator ejector shown in 6B, and the combination of the pusher and ejector shown in 6C;

FIG. 7 is an elevational view of the auxiliary stop also showing its alternate position in ghost lines;

BEST MODE FOR CARRYING OUT THE INVENTION

The unique characteristics of the present invention, which are explained in detail below, are the shape and operation of the protective head which is shaped to stretch the skin taut as the needle is injected so that little or no pain is encountered when injection occurs. The safety cam action of the piston assembly automatically pulls the syringe back off the stop which determines visual presence of blood in the syringe. Signs of blood show that the needle is in the wrong place for injection. Further proof of wrong placement is shown when the piston assembly is released and it automatically pulls itself back to the piston assembly slot side of the apparatus. When the syringe needle is in a correct location, the piston assembly will stay on the opposite side of the apparatus showing that it is safe to inject the fluid. The locking-in of the syringe into the elevator ejector, the ability to load several medications into one syringe, the base 200 which allows vertical upright and out-of-the-way storage, and the elevator pusher which allows a horizontal side laydown position so as to enable the apparatus to drip dry after sterilizing.

Figure 1:
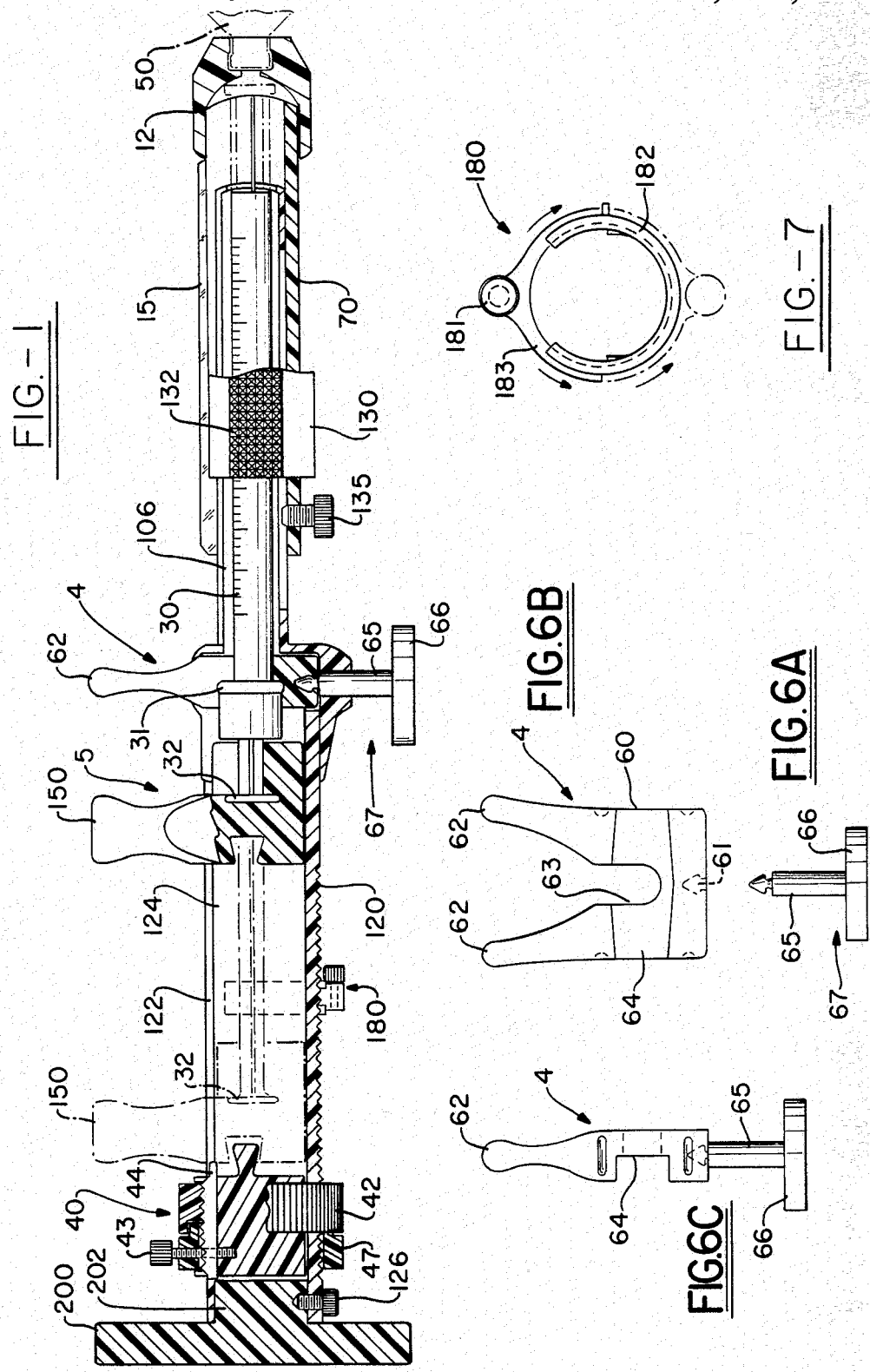
FIG. 1 is an enlarged elevational view, in partial cross-section, illustrating the self-injection apparatus comprising the invention.
Figure 2:
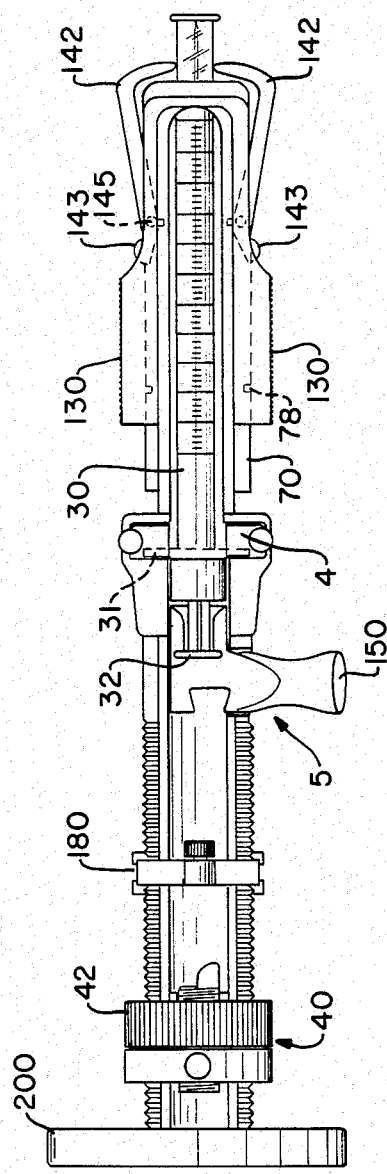
FIG. 2 is a top view of the apparatus illustrating the syringe and needle protector position upon insertion into the apparatus.
Figure 3:
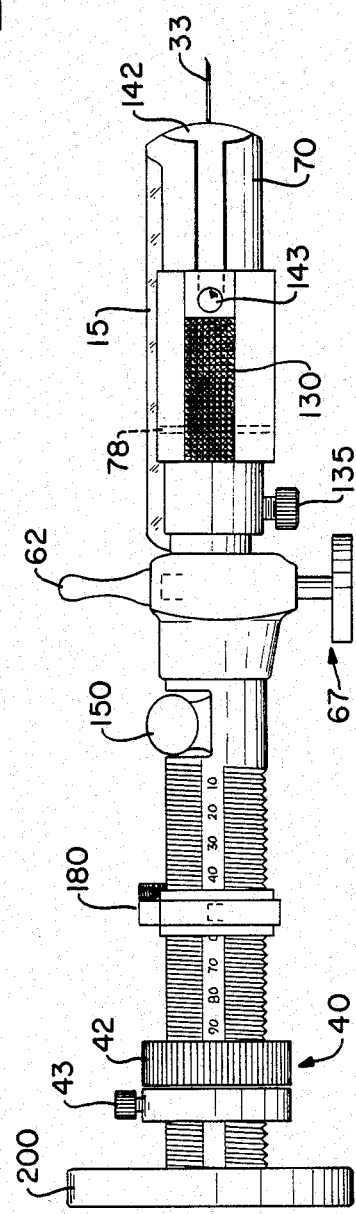
FIG. 3 is a side elevational view of the apparatus with the needle protector removed.

In FIG. 1, the self-injection apparatus does not at first contain the syringe nor is the standard medical fluid vial attached. It will now be explained how the apparatus is loaded and how it functions.

First, the injection apparatus is taken off of its base 200. Base 200 is unique in that it allows the apparatus to be stored in an upright position. Base 200 can be circular, rectangular, or triangular, with an outward cylindrical protrusion 202 that fits snuggly into the stopper sleeve end.

A standard disposable hypodermic syringe 30 is obtained. Holding the injection apparatus in one hand and pushing up on the elevator pusher 67 with the same hand and taking the syringe in the other hand, the loading procedure is ready to begin.

In FIG. 6, the elevator pusher 67 is comprised of a cylindrical, rectangular, triangular, and the like, shaft 65, which is attached, at its lower extremity, by conventional means, to a base 66. Said base is in the shape of a rectangle, circle, triangle, or the like. The upper extremity of the shaft 65 is in a trapezoidal, rectangular, triangular, or the like, shape which serves as a key to lock the shaft 65 into the elevator ejector keyway 61. This key secures the elevator pusher 67 into the elevator ejector 4.

Pushing up on the elevator pusher 67 causes the elevator ejector 4 to become elevated. With the elevator ejector 4 elevated, the syringe 30, with needle protector still on, is slid through the elevator ejector 4, with the cubic centimeter scale of the syringe pointing up, into the nose sleeve (inner) cavity 106 of the main body.

The elevator ejector 4, as shown in FIG. 6, is a one-piece construction, horseshoe-shaped apparatus with enlarged horns 62 on the extremeties of both legs of the horseshoe. The elevator ejector body 60 has a circular indentation 63 to enable a syringe to rest snuggly in the indentation. Also, in the body 60, are syringe-firm notches 64, said notches 64 being of a rectangular shape. Said notches 64 enable the arms 31 of the syringe 30 to lock into the elevator ejector 4, thus securing the syringe in the apparatus. The elevator ejector body 60 has a keyway 61 located in the bottom center of the device which enables the elevator pusher 67 to be secured into the elevator ejector 4. The size of the elevator ejector 4 will vary with the size of syringe used.

Figure 13:
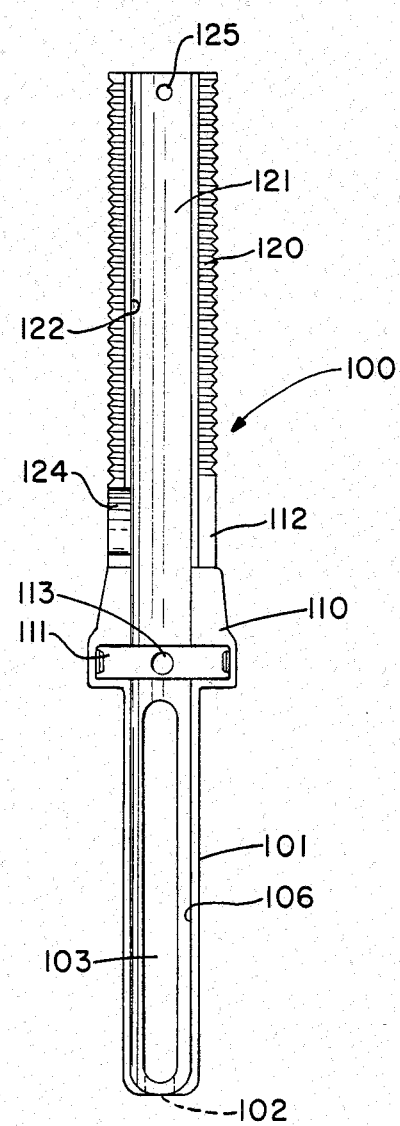
FIG. 13 is a top view of the main body of the self-injection apparatus absent the sub-assemblies.

As shown in FIG. 13, main body 100 is a one piece construction divided into three sections and is of a cylindrically shaped tube, varying in size to accommodate standard disposable syringe sizes. Syringe sizes vary from 50 units or ½ cc to about 100 units or 1 cc. The nose sleeve 101, being the upper third of the main body 100, is comprised of an inner sleeve cavity 106, a front aperture 102, a top channel 103, said inner sleeve cavity 106 is in the inside portion of the nose sleeve 101, this is where the syringe rests when the apparatus is in use. Top channel 103 enables the syringe to be slid into the inner sleeve cavity 106 and also aids in the visualization of the syringe to protrude out of the apparatus. The housing 110, being the middle third of main body 100, is comprised of the open elevator ejector housing 111 and the open piston assembly housing 112. The elevator ejector housing 111 is rectangular in shape, allowing the elevator ejector to slide freely within, while fitting snuggly in the housing 111. Also, there is an aperture 113 in the housing 111 to enable the elevator pusher shaft 67 to slide freely into the housing 111. The piston assembly housing 112 is cylindrical in shape and allows the piston assembly 150 to slide freely within. The stopper sleeve 120, being the bottom third of the main body 100, is comprised of an inner sleeve 121, a top channel 122, a piston assembly slot 124, a thread exterior with numerical scale, and a stop screw aperture 125. The inner sleeve 121 enables the piston assembly 150 to slide back and forth until it comes in contact with a dosage stop 40. The top channel 122 enables the visualization of the piston assembly and allows the dosage stop 40 to be slid into the inner stopper sleeve 121 for securement. Piston assembly slot 124 enables the piston assembly 150 to rest and be stationary for the loading process. Stopper sleeve 120 is threaded on its exterior so that the dosage stops can be fine tuned to specified dosage. A scale is provided on the exterior of the stopper sleeve 120 so that the user can judge the amount of medication that has been taken into the syringe. The stop screw aperture is of a standard desired size and a screw 126 is placed in said aperture so that dosage stops will not come off. All components are sized according to the size of the standard disposable syringe used.

While the syringe 30 is resting in the inner sleeve cavity 106, the outer needle guide adjuster 130 is turned counter-clockwise thus freeing the needle guide 140.

Figure 10B:
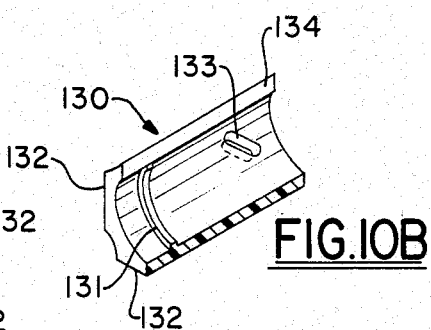
FIG. 10 shows the outer needle guide adjuster in a frontal elevational view at 10A and in a crosssectional perspective view at 10B.
Figure 10A:
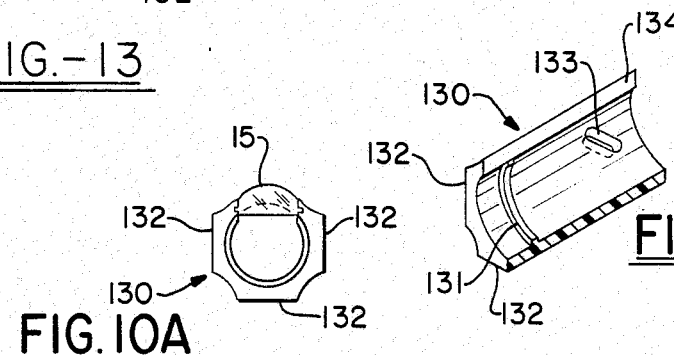

As shown in FIG. 10, outer needle guide adjuster 130 is a cylindrically-shaped sleeve that is mounted to outer sleeve 70 which in turn slides over the nose sleeve 101 of the main body 100. Said outer needle adjuster 130 includes an inner ring 131, three protruding gripping surfaces 132, side slots 133, a drag screw 135, and a top channel 134. Said outer sleeve 70 is a cylindrical tube which fits over said nose sleeve 101. Said outer needle guide adjuster 130 then slides over said outer sleeve 70. Said outer sleeve 70 is comprised of pivot and needle guide slots 72, drag screw perforation 76, and a bottom channel 74. Said slots 72 enable the needle guides 140 to pivot in and out as desired and to come to a fully opened and fully closed position. Said drag screw perforation allows the drag screw 135 to apply needed friction to said nose sleeve 101. Said bottom channel 74 allows light into the assembly for increased visibility of the syringe 30. Said inner ring is a circular protrusion on the inside of said outer needle guide adjuster 130 to enable it to rotate into the desired position. Gripping surfaces 132 are at right angles with respect to one another and enable better handling of the device. Side slots 133 enable the needle guide 140 to move freely in said adjuster 130. Drag screw 135 applies the necessary friction to the outer sleeve 70 to allow said outer needle guide adjuster 130 and said outer sleeve 70 to slide up and down said nose sleeve 101 at desired velocities. Top channel 134 is the cut-out portion on the top of the outer needle guide adjuster 130. This enables the user to insert the magnifier 15 so that he can read the scale on the syringe.

Figure 11:
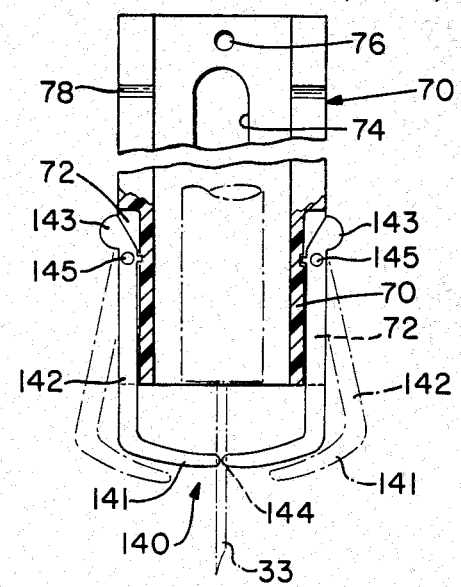
FIG. 11 is a plan view of the needle guide and guide sleeve showing the needle guides in closed position with respect to the syringe needle shown in ghost lines and in an alternate open position also via ghost lines.

As shown in FIG. 11, needle guides 140 comprise a head 141, neck 142, pivot 145, and button 143. Head 141 is flat and can be smooth or ridged, thus enabling the needle guides 140 to tension the skin surface so that minimum pain is felt when the needle is injected into the skin. Neck 142 is the straight portion connecting the head 141 to the button 143. Said pivot 145 enables said guides 140 to pivot in and out as desired. Buttons 143 are protrusions which aid in the opening and closing of the needle guides 140 for the loading and unloading of the syringe. Opening is accomplished by a counter-clockwise rotation of the outer needle guide adjuster 130 and pushing in on the buttons. Closing is accomplished by a clockwise rotation of the outer needle guide adjuster 130, thus pushing the buttons back out to their normal position. After opening, the syringe 30, with protective cover still in place, is slid into the inner sleeve cavity 106 until the syringe arms 31 come into contact with the elevator-ejector grooves 64. The piston assembly 150 is slid into place in the main body slot 124.

Figure 9:
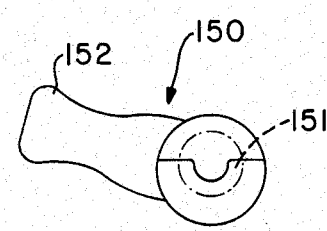
FIG. 9 is a frontal elevational view of the piston assembly.

Piston assembly 150 of FIG. 9 is cylindrically shaped and is sized to fit firmly in the inner sleeve 122 of the stopper sleeve 120. Piston assembly 150 comprises a plunger slot 151 and assembly arm 152. Plunger slot 151 is indented into assembly 150 so that the syringe plunger end 32 fits snuggly into said slot 151. The assembly arm 152 protrudes out of said assembly 150, and is fastened to said assembly 150 by conventional means, and enables said assembly 150 to be slid up and down said inner sleeve 122 of the stopper sleeve 120.

The elevator ejector 4 is then pushed down with the syringe plunger end 32 going into a plunger slot 151 into the piston assembly 150, thus locking the syringe into the elevator ejector 4. The magnifying cover 15 is snapped on top of the outer needle guide adjuster 130 so as to magnify the number on the syringe 30.

As depicted in FIG. 1, magnifying cover 15 is made of any standard magnifying material, with its size varying according to the size of the apparatus. Cover 15 is of a rectangular shape with a slight curvature to enable it to fit over the channel 134 on the outer needle guide adjuster 130.

Figure 5:
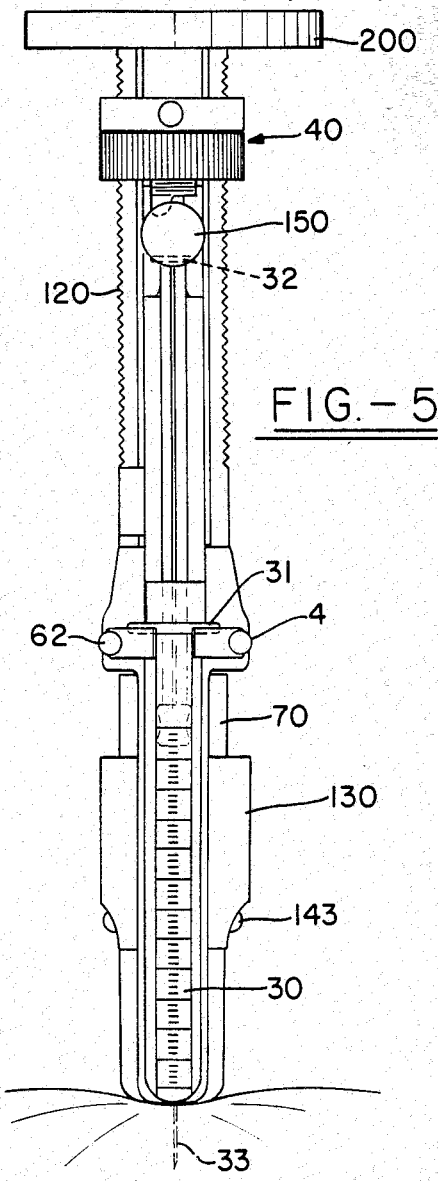
FIG. 5 illustrates the syringe needle position after injection but prior to serum injection.

The piston assembly 150 is slid back until it comes into contact with the dosage stop 40, as shown in FIG. 5. The syringe 30 is now full of air. The needle protector is now removed. The outer needle guide adjuster 130 is now turned clockwise, thus closing the needle guides 140 around the sterile needle 33. The needle 33 protrudes approximately 10 to 15 one-thousandths of an inch outside of said needle guides 140. The guide end, with the exposed needle 33 protruding therefrom, is now dipped into a container containing some form of antiseptic such as cotton balls drenched in isopropyl alcohol. After the alcohol dip and drip drying, the medical fluid vial 50 is attached to the vial adapter 12, said adapter 12 is then placed over the needle guide end of the apparatus.

Figure 12:
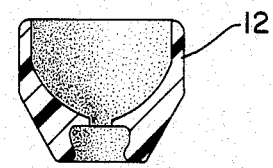
FIG. 12 is a cross-sectional elevational view of the vial adapter.

Vial adapter 12, as shown in FIG. 12, is a uniquely designed conically shaped device. The larger of the ends is designed to fit over the needle guide end of the apparatus and therefore is sized accordingly, while the smaller of the ends is designed to fit snuggly over a standard medical vial.

Figure 8A:
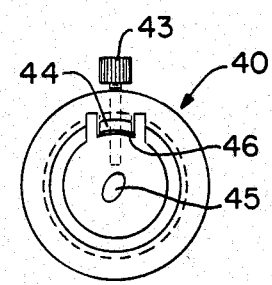
FIG. 8 shows the dosage stop in frontal elevational view at 8A and in a side elevational view at 8B.
Figure 8B:
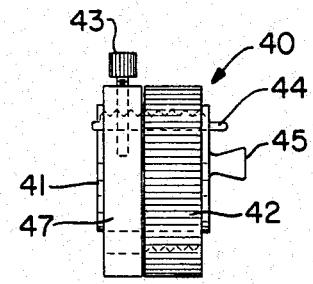

As shown in FIG. 8, dosage stop 40 is a cylindrical collar which is slid onto the stopper sleeve 120. The size of the dosage stop 40 varies with the size of the apparatus. The dosage stop 40 is comprised of a locking collar 41, fine adjustment nut 42, adjustment screw lock 43, and fine tuning rod 44. The locking collar 41 is cylindrically shaped with an inner projection 45 which slides into said stopper sleeve channel 121 and is housed in said inner sleeve 122. Said collar 41 has a rectangular slot 46 which enables the fine tuning rod 44 to slide back and forth. Said collar 41 also has an outer ring 47 which secures the collar 41 onto the stopper sleeve 120. Also, there is an aperture in the top of said collar 41 which is mounted to said adjustment screw lock 43, this device securing the collar 41 to the stopper sleeve 120. Fine adjustment nut 42 is a circular ring threaded on the inside, which is attached to said collar by conventional means. Said nut 42 rotates back and forth on the thread of the rod 44 which results in the fine tuning adjustment of rod 44. Rod 44, depicted in FIG. 8, is attached to said collar 41 by conventional means. Rod 44 is an L-shaped design, slightly arched, being threaded on the top side, which enables it to be moved back and forth in accordance with the turning of the fine adjustment nut 42. The rod slides back and forth through said slot 46 in said collar, thus enabling the apparatus to be finely adjusted.

The outer needle guide adjuster 130 is now slid down the nose sleeve 101 until it comes in contact with the elevator ejector housing 111. Once this occurs, the needle 33 is inside of the medical fluid vial 50. The piston assembly 150 is then slid upwardly until it contacts the elevator ejector housing 111, thus forcing the air in the syringe 30 into the medical fluid vial 50. The piston assembly 150 is then slid back down the inner sleeve 121 until it comes into contact with the dosage stop 40, thus loading the syringe 30 for the injection.

However, in some instances, some patients require two different types of medication to be taken at one time from the same syringe. The apparatus is equipped with an auxiliary dosage stop 180 (FIG. 7), which also has a fine adjustment screw 181. The auxiliary dosage stop 180 is comprised of a collar ring 182, a straddler 183, and fine adjustment screw 181. Collar ring 182 is threaded on the inside so that it may move back and forth on the threaded stopper sleeve. Straddler 183 is attached to said collar ring 182 by conventional means and is a U-shaped design with a protrusion in the center with an aperture for housing of the fine adjustment screw 181. The straddler 183 is unique in that it has the ability to be slid up and down and out of the way as set forth hereinbelow. The adjustment screw is of a standard size with a machined head. This auxiliary dosage stop; 180 is unique in that the top part, which straddles the top channel 122 slides up to allow the piston assembly 150 to pass back so that the air can be forced into the vial as previously set forth hereinabove. Thus, the auxiliary dosage stop 180 can be used for the fist medical fluid, slid down, then a second medical fluid vial can be attached on the needle guide end, and then the second medical fluid can be loaded into the syringe 30.

After the syringe is loaded with fluid, the vial 50 and the adapter 12 are removed, and the outer needle guide adjuster 130 is then slid up the nose sleeve 101 to its original position. Now, with the needle guide 140 surrounding the protruding needle, the apparatus is ready for the injection procedure.

Figure 4:
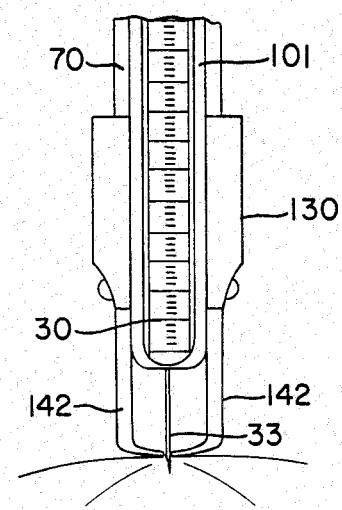
FIG. 4 illustrates the syringe needle position prior to injection.

After the area to be injected has been cleaned with an antiseptic such as isopropyl alcohol, the procedure is ready to begin. The syringe now loaded and with the piston assembly 150 against the dosage stop 40 with the claw end of the apparatus placed on the clean injection surface, the procedure can be commenced (See FIG. 4). The needle guides 140 are unique in that they pull at the skin in all directions so when the needle 33 is injected into the patient, there is only a minimum discomfort to the patient. With the needle guide now placed on the skin surface, the apparatus is then pushed downward, forcing the outer sleeve 70 to slide up the nose sleeve 101 until it comes into contact with the elevator ejector housing 111, thus thrusting the needle 33 into the skin (FIG. 5). The piston assembly 150 is now turned counter-clockwise to the side opposite of the piston assembly slot 124 of the apparatus. This cam action of the piston assembly 150 and the design of the fine adjustment rod 44, causes the syringe 30 to suck in some of the body fluid. This is important for the injection of insulin due to the fact that all insulin is to be injected into the adipose tissue and not into the blood vessels. After the syringe 30 is checked, and no blood appears, then the piston assembly 150 is pushed down the inner cavity 122 until the piston assembly 150 comes into contact with the piston assembly housing 112, ending the stroke, thus forcing the fluid into the patient.

After this is accomplished, the apparatus is removed from the patient. The piston assembly is turned clockwise until it is into the piston assembly slot 124 and the elevator pusher 67 is then pushed up, ejecting the syringe 30. The syringe 30 is taken out of the apparatus and is disposed of in a proper trash receptacle.

All identified componets vary in size according to the size of standard syringe desired. Further, changes can be made in the size, shape, and construction of the device disclosed herein without departing from the spirit and scope of the present invention.

While in accordance with the patent statutes, only the best mode and preferred embodiments of the invention has been set forth, the scope of the invention is measured by the appended claims.

What is claimed is:

1. A manual syringe injection apparatus, comprising:
   a cylindrical tube;
   a cylindrical needle guide attached to said tube by a sliding means at one end of said tube, said needle guide separating upon contact with a surface to tension such surface;
   an elevator ejector attached to said tube in the center section of said tube; and
   a piston assembly inserted inside of the other end of said tube, wherein a syringe is locked into said tube by said elevator ejector.

2. A manual syringe injection apparatus in claim 1, wherein a pair of needle guides are attached to said outer needle guide adjuster to aid in loading and injecting of said syringe and in tensioning recipient surface.

3. A manual syringe injection apparatus in claim 2, wherein said tube comprises:
   a nose sleeve section;
   a housing section; and
   a stopper sleeve section threaded on its outer perimeter.

4. A manual syringe injection apparatus in claim 3, wherein said outer needle guide adjuster is attached to an outer sleeve and nose section and said elevator ejector is attached to said housing section and said piston assembly is inserted into said stopper sleeve section.

5. A manual syringe injection apparatus in claim 3, wherein a dosage stop and an auxiliary dosage stop are attached to said stopper sleeve section.

6. A manual syringe injection apparatus comprising:
   a hollow conical vial adapter, wherein said adapter has one end that attaches to a standard medical vial and the other end attaches to the apparatus of claim 1.

* * * * *